(12) United States Patent
Vidal et al.

(10) Patent No.: US 8,409,592 B2
(45) Date of Patent: Apr. 2, 2013

(54) WHEY AND THYMUS FUNCTION

(75) Inventors: Karine Vidal, Lausanne (CH); Eric Delpierre, Nogent-s/Marne (FR); Cecile Loi, Creteil (FR); Christophe Moinard, Bourg la Reine (FR); Christine Charrueau, Athis Mons (FR); Denis Breuille, Lausanne (FR); Luc Cynober, Sceauz (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/120,118

(22) PCT Filed: Sep. 14, 2009

(86) PCT No.: PCT/EP2009/061876
§ 371 (c)(1),
(2), (4) Date: Jun. 1, 2011

(87) PCT Pub. No.: WO2010/031744
PCT Pub. Date: Mar. 25, 2010

(65) Prior Publication Data
US 2012/0039944 A1    Feb. 16, 2012

(30) Foreign Application Priority Data
Sep. 19, 2008 (EP) .................... 08105395

(51) Int. Cl.
*A61K 39/00* (2006.01)

(52) U.S. Cl. ...... 424/278.1; 424/535; 514/1.1; 514/19.3
(58) Field of Classification Search ........................ None
See application file for complete search history.

(56) References Cited

U.S. PATENT DOCUMENTS

| 5,576,351 A | * | 11/1996 | Yoshimura et al. | 514/565 |
| 5,728,678 A | * | 3/1998 | Trimbo et al. | 514/5.5 |
| 5,952,193 A | * | 9/1999 | Shimamura et al. | 435/68.1 |
| 6,656,903 B1 | * | 12/2003 | Sawatzki et al. | 514/7.6 |
| 6,833,350 B2 | * | 12/2004 | Ballevre et al. | 514/2.4 |

FOREIGN PATENT DOCUMENTS

| EP | 1048226 A1 | * | 11/2000 |
| WO | WO 9949741 A1 | * | 10/1999 |
| WO | WO 03007730 A1 | * | 1/2003 |

OTHER PUBLICATIONS

Goldman et al., Advances in Pediatrics, 1985, 32:71-100.*
Zimmerman et al., J Family Practice, 2003, 52:s1-s21.*
Janeway et al., Immunobiology, 3rd edition, 1997, Garland Publishing, pp. 6:4-6:5.*
Kennedy et al., Anticancer Res. Nov.-Dec. 1995;15(6B):2643-9.*
Maev et al., Eksp Klin Gastroenterol. 2003;(3):100-6. (abstarct only).*
Lykhach et al., Klin Khir. Jul. 2004;(7):5-7. (abstract only).*
Merck Manual of Diagnosis and Therapy, 17th edition, 1999, pp. 1143-1147.*
Aspinal, R, . J Immunol. Apr. 1, 1997;158(7):3037-45.*
Aspinal et al., Springer Semin Immunopathol. 2002;24(1):87-101.*
Hale et al., Dev Comp Immunol. Jun.-Jul. 2001;25(5-6):509-18.*
Singh et al., Clin Exp Immunol. Sep. 1979;37(3):507-11.*

* cited by examiner

*Primary Examiner* — Michael Szperka
(74) *Attorney, Agent, or Firm* — K&L Gates LLP

(57) ABSTRACT

The present invention generally relates to the field of nutrition and health. In particular, the present invention provides a composition that can be used to maintain or improve thymus health. One embodiment of the present invention is the use of whey or at least one protein fraction thereof for the preparation of a composition to maintain or improve thymus function.

33 Claims, 1 Drawing Sheet

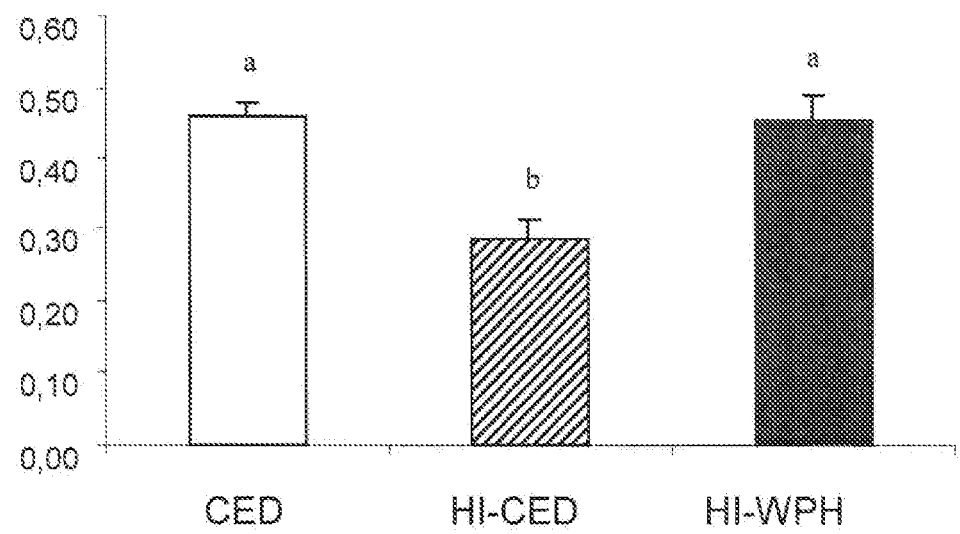

WHEY AND THYMUS FUNCTION

The present invention generally relates to the field of nutrition and health. In particular, the present invention provides a composition that can be used to maintain or improve thymus health and/or function. One embodiment of the present invention is the use of whey or at least one protein fraction thereof for the preparation of a composition to maintain or improve thymus health and/or function.

The thymus gland has many important functions, for example it is a key player for a powerful immune system. The thymus is the organ responsible for the generation of functional T cells. One role of the thymus is the education (differentiation and maturation) of T lymphocytes, resulting in a negative selection of autoreactive T cells and a positive selection of useful T cells (Marrack et al. 1998. Cell 53:627; Lo et al. 1997. Immunol Res 16:3; Anderson et al. 1996. Annu Rev Immunol 14:73).

Although the thymus continues to develop after birth and reaches its maximal size during puberty, a gradual shrinking of the thymus, called involution, occurs steadily with age after puberty (Linton & Dorshkind 2004 Nat Immunol 5:133). This thymic involution is a normal process which occurs for example early and progressively during the aging process. The thymus undergoes profound changes in its anatomy associated with loss of thymic epithelial cells and a decrease in thymopoiesis. This decline in the output of newly developed T cells results in diminished number of circulating naïve T cells and impaired cell-mediated immunity.

In addition to the age-related thymic involution (i.e. chronic thymus atrophy), the thymus also shows a reversible involution (i.e. acute thymus atrophy) in response to various physiological or pathological conditions (Taub & Longo 2006 Immunological Reviews 205:72). For instance, alterations in thymocyte numbers and thymic size have been reported during pregnancy, various inflammation conditions, bacterial and viral infections, physical and emotional stress, malnutrition, chemotherapy and exposure to toxin.

A compromised immune response contributes to poor health, fatigue and many disease states. The ability to regenerate the thymus represents, hence, one of the major challenges of modern medicine. This strategy will have applications in a wide range of life threatening diseases including immunodeficiency, cancer and autoimmunity; severe infections including AIDS; and in anti-aging applications. This strategy can help in various conditions such as increasing the efficacy of vaccines; reversal of immunosuppression states such as post-chemotherapy/radiation therapy; organ transplantation; restoration of a specific anti-tumour immune response; restoration of a specific antimicrobial immunity e.g. bacteria, virus, fungi, parasites; normalisation of T cell immunodysregulation states e.g. autoimmunity (multiple sclerosis, lupus rheumatoid arthritis), allergy, and dermatitis/psoriasis.

Different approaches have been tested to maintain thymus health during aging. It has been reported that thymic tissues and bone marrow transplantation, and thymus extract administration can help reversing the effect of age-related thymic involution and immune system weakening (Kouttab et al. 1989. Med Oncol Tumor Pharmacother. 6:5; Pandolfi et al. 1983 Thymus. 5:235; Dabrowski et al. 1987 Ann N Y Acad Sci 496:697; Valesini et al. 1986 Eur J Cancer Clin Oncol. 22:531)

More recently, systemic administration of cytokines (e.g. IL-7) and hormones (e.g. GH, IGF-1) have resulted in increased thymic activity and T-cell output with age (Henson et al., Exp Gerontol. 2004 39:673; Virts et al., 2006 Rejuvenation Res. 9:134).

Some nutritional approaches, such as oral administration of zinc (et al., 1993 Clin Immunol Immunopathol. 66:127; Mocchegiani et al., 1995 Int J. Immunopharmacol. 17:703) have also been reported to improve to some extent the thymic function. Combination of Zinc and sodium diethyldithiocarbamate given 10 days prior a stress model in mice restored stress-impaired thymus weight and immune function (Obminska-Mrukowicz et al., 2005 J Vet Sci. 6:25).

However, excessive Zn-supplementation may have disadvantages. A recent review reported that although Zn is considered to be relatively nontoxic, manifestations of overt toxicity symptoms (nausea, vomiting, epigastric pain, lethargy, and fatigue) will occur with high zinc intakes. At low intakes, but at amounts in excess of the Recommended Dietary Allowance (RDA), for example of 100-300 mg Zn/day, evidence of induced copper deficiency with attendant symptoms of anemia and neutropenia, as well as impaired immune function and adverse effects on the ratio of low-density-lipoprotein to high-density-lipoprotein (LDL/HDL) cholesterol have been reported. Even lower levels of zinc supplementation, closer in amount to the RDA, have been suggested to interfere with the utilization of copper and iron and to adversely affect HDL cholesterol concentrations (Fosmire, American Journal of Clinical Nutrition. 51:225).

It was consequently the object of the present invention to provide the art with a nutritional approach to maintain or improve thymus health, to protect the thymus from induced involution and/or to accelerate thymopoeisis that uses natural ingredients and that overcomes the disadvantages of the methods listed above.

The present inventors were surprised to see that they could achieve this object by a use in accordance with claim 1.

Hence, the present invention relates to a composition comprising whey or at least one protein fraction thereof for use in maintaining and/or improving thymus function and/or thymus health.

The inventors have investigated the ability of a whey-based nutrition to restore the thymus weight and function in an experimental model of head-injury inducing thymus atrophy.

The metabolic response to head injury (HI) is characterized by a dysimmunity which is a risk factor, for example, for secondary infection and potentially sepsis. A feature seen in HI is a severe atrophy of the thymus. The thymus is a primary lymphoid organ in which T cells undergo differentiation leading to a migration of positively selected thymocytes to the T-cell dependent areas of peripheral lymphoid organs.

By using a rat model of HI by fluid percussion, it could be shown that a whey-based diet was able to reverse the thymus atrophy.

The whey-based diet is hence beneficial in maintaining or improving thymus health and lymphocyte function.

A whey-based diet is any diet comprising whey or at least one protein fraction thereof.

Consequently, one embodiment of the present invention is the use of whey or at least one protein fraction thereof for the preparation of a composition to maintain or improve thymus function and/or health.

Whey or at least one protein fraction thereof may also be used for the preparation of a composition to maintain or improve lymphocyte function and/or the immune system. They may also be used for the preparation of a composition to treat or prevent lymphocytopenia.

While the thymus usually reaches full size at the stage of puberty, it tends to shrink thereafter. Thymus atrophy is consequently a well-known condition occurring for example with age. The consequence of this atrophy is—as discussed above—that while the stock of T-lymphocytes is built up early in life, this function diminishes in adults.

Consequently, in one embodiment the composition prepared by the use of the present invention is intended for consumption after puberty, in particular by adult and/or elderly subjects.

Thymus atrophy may also occur in response to various physiological or pathological conditions, such as for example various inflammation conditions, bacterial and viral infections, physical and emotional stress, chemotherapy and/or exposure to toxins.

The thymus size appears also to be dependant on the nutritional status. Malnutrition may lead to a reduced thymus size and activity.

Consequently, the composition prepared by the use of the present invention may successfully be applied in particular to subjects with an impaired health, for example in all the conditions mentioned above. It may also be used as a preventive measure, for example for subjects at risk of developing an impaired health.

Further, while at the time of birth, the human immune system is still immature, within the first year of life the thymus acts crucially in the maturation of the T-lymphocytes, for example, by serving to differentiate the immature T-lymphocytes to immune competent T-lymphocytes.

The composition prepared by the use of the present invention may consequently also be used to support thymus growth and/or the maturation of the immune system, during infancy. It may also be consumed during pregnancy by the mother to support thymus growth and/or the maturation of the immune system of the infant.

Thymus atrophy also plays a role in a wide range of life threatening diseases including immunodeficiency, cancer and autoimmunity; severe infections including AIDS; and consequently, the composition of the present invention may be applied in these conditions.

The composition may further be used to increase the efficacy of vaccines; to reverse immunosuppression states such as post-chemotherapy/radiation therapy; to support organ transplantation; to restore anti-tumour immune responses; to restore antimicrobial immunity e.g. against bacteria, virus, fungi, parasites; and/or to normalise T cell immunodysregulation states e.g. in autoimmunity, such as multiple sclerosis, or lupus rheumatoid arthritis, allergy, and/or dermatitis/psoriasis.

The composition described in the present invention may be used to maintain or re-establish lymphocyte function and/or to treat or prevent thymus atrophy.

It may further be used to boost the immune system, in particular to improve immune response during the aging process.

Further, the composition may be used maintain or improve thymus function and/or health in a state of obesity; immune deficiency, for example after chemotherapy or HIV infection; autoimmune disorders, for example systemic lupus erythematosus (SLE), multiple sclerosis (MS) or dermatomyositis (DM); stress, for example chronic or social stress; infections, for example such as bacterial or viral infections; toxication; or combinations thereof.

Generally, the composition of the present invention may be applied to any organism that has a thymus. Preferably the composition prepared by the use of the present invention is intended for humans, pets, companion animals and/or livestock.

It may be used for oral, enteral, topical or parenteral administration.

The composition may be provided in any form suitable for consumption. Preferably, the composition may be a medicament, a food product, a pet food product, a food additive, a nutraceutical or a drink.

Whey-based formulations were found to have the described effects. Any formulation comprising or consisting of whey, whey proteins or fractions thereof may be used.

The protein fraction in whey (approximately 10% of the total dry solids within whey) comprises four major protein fractions. These are beta-lactoglobulin, alpha-lactalbumin, bovine serum albumin and immunoglobulins.

If whey protein is used, the source of the whey protein may be acid whey, sweet whey, whey protein isolate or mixtures thereof. Preferably, however, the protein source is based on whey protein isolate or modified sweet whey. Sweet whey is a readily available by-product of cheese making and is frequently used in the manufacture of infant formulas based on cows' milk.

The whey or whey protein may be obtained for example from human, bovine, sheep, goat or camel sources.

In one embodiment, the whey protein fraction is at least in part enzymatically hydrolyzed whey protein. Consequently, whey protein hydrolysate may be used as whey protein fraction. Whey protein hydrolysate is readily commercially available from several sources. One possible example of a whey protein hydrolysate (WPI) is Peptamen®, optainable from Nestlé Nutrition.

Using hydrolysed whey protein has for example the advantage, that this protein fraction is hypoallergenic. Typically, hypoallergenic hydrolysed whey protein may have a degree of hydrolysis (DH) of between 8 and 20, more preferably between 9 and 16. A particularly preferred degree of hydrolysis is 14. The whey protein may be hydrolysed in any suitable manner known in the art, for example as described in European Patent No. 322,589, the contents of which are incorporated herein by reference. If the whey fraction used as the starting material is substantially lactose-free, it is found that the protein suffers much less lysine blockage during the hydrolysis and subsequent thermal processing. This enables the extent of lysine blockage to be reduced from about 15% by weight of total lysine to less than about 10% by weight of lysine; for example about 7% by weight of lysine blockage which greatly improves the nutritional quality of the protein source.

"Degree of hydrolysis" (DH) means the percentage of nitrogen in the form of free alpha-amino nitrogen as compared to total nitrogen as measured by the TNBS method described by Adler-Nissen et al. in "Determination of the Degree of Hydrolysis of Food Protein Hydrolysates by Trinitrobenzenesulfonic acid" (J. Agric. Food Chem. 1979. 27:1256). It is a measure of the extent to which a protein has been hydrolysed.

The whey or the at least one protein fraction thereof may further be supplemented, for example with those amino acids in respect of which it has a low content (principally histidine and arginine). Consequently, the whey or the at least one protein fraction thereof, for example sweet whey or whey protein isolate, may be supplemented with free arginine in an amount of from 0.1 to 3% by weight of the total protein content of the composition and/or free histidine in an amount of from 0.1 to 3% by weight of the total protein content of the composition.

The whey may also be supplemented in various amino acids for which an increased requirement associated to pathological conditions was demonstrated. This is of particular importance if the composition of the present application is to be applied in diseases conditions. For instance in EP94 402 420 "Composition à base d'acides amines pour le traitement d'infections" the benefit of a diet enriched in Cysteine, Threonine, Serine and aspartate/asparagine and in EP1638418 "Amino acids supplementation to restore intestinal flora", the benefit of a mix of Threonine, Serine, Proline and cysteine was demonstrated. Moreover, it is well known that glutamine is important (conditionally indispensable amino acids) in a number of pathological conditions and thus it may be also of interest to add glutamine to whey since whey does not contain high glutamine level.

For example, the whey protein fraction may contain arginine in the range of 2-3 weight-% of the total protein content of the composition.

If however the arginine content is too high, this may have a negative impact on the flavour of the final composition.

The whey or at least one protein fraction thereof preferably represents at least 30 weight-%, preferably at least 50 weight-%, more preferred at least 70 weight-%, even more preferred at least 90 weight-% and mostly preferred at least 95 weight-% of the total protein content of the composition.

Preferably, the composition contains minerals in amounts corresponding to no more than 100% of the maximum recommended level of daily mineral intake per 100 g whey protein.

It may also contain minerals in amounts corresponding to no more than 100% of the maximum recommended level of daily mineral intake per daily dose.

For example, in a preferred embodiment, the composition may contain less than 35 mg zinc per 100 g whey protein.

The table below presents the recommended daily intake and the maximum recommended level of daily mineral intake for Zinc for healthy people. The table represents information taken from Dietary Reference Intakes for Calcium, Phosphorous, Magnesium, Vitamin D, and Fluoride (1997); Dietary Reference Intakes for Thiamin, Riboflavin, Niacin, Vitamin B6, Folate, Vitamin B12, Pantothenic Acid, Biotin, and Choline (1998); Dietary Reference Intakes for Vitamin C, Vitamin E, Selenium, and Carotenoids (2000); and Dietary Reference Intakes for Vitamin A, Vitamin K, Arsenic, Boron, Chromium, Copper, Iodine, Iron, Manganese, Molybdenum, Nickel, Silicon, Vanadium, and Zinc (2001). These reports may be accessed via www.nap.edu provided by The National Academies.

| Life Stage Group | Recommended daily Zn intake (mg/d) | maximum recommended level of daily Zn intake (mg/d) |
|---|---|---|
| Infants | | |
| 0-6 months | 2 | 4 |
| 7-12 months | 3 | 5 |
| Children | | |
| 1-3 years | 3 | 7 |
| 4-8 years | 5 | 12 |
| Males | | |
| 9-13 years | 8 | 23 |
| 14-18 years | 11 | 34 |
| 19-30 years | 11 | 40 |
| 31-50 years | 11 | 40 |
| 50-70 years | 11 | 40 |
| >70 years | 11 | 40 |
| Females | | |
| 9-13 years | 8 | 23 |
| 14-18 years | 9 | 34 |
| 19-30 years | 8 | 40 |
| 31-50 years | 8 | 40 |
| 50-70 years | 8 | 40 |
| >70 years | 8 | 40 |
| Pregnancy | | |
| ≦18 years | 12 | 34 |
| 19-30 years | 11 | 40 |
| 31-50 years | 11 | 40 |
| Lactation | | |
| ≦18 years | 13 | 34 |
| 19-30 years | 12 | 40 |
| 31-50 years | 12 | 40 |

The composition may consist of protein only. It may however also comprise a lipid fraction and/or a carbohydrate fraction. Lipids and carbohydrates may have a positive impact, for example on taste and mouthfeel. They also contribute significantly to the nutritional profile of the composition.

If the composition is a food product, for example a nutritional composition such as a complete nutritional composition, a functional food, a feeding formula, a functional food or a nutraceutical, it is preferred if the composition contains next to the whey or whey protein fraction also a carbohydrate fraction and a lipid fraction.

For example, the whey or the at least one protein fraction thereof may be comprised in the composition in an amount that corresponds to about 5-100% of the calories of the composition, preferably about 7-50% of the calories of the composition, even more preferred about 10-30% of the calories of the composition are derived from whey protein.

The carbohydrate fraction may be comprised in the composition in an amount that corresponds to about 5-100% of the calories of the composition, preferably about 10-90% of the calories of the composition, even more preferred about 40-85% of the calories of the composition are derived from carbohydrates. Any suitable carbohydrate may be used, for example sucrose, lactose, glucose, fructose, corn syrup solids, maltodextrins, and mixtures thereof. The carbohydrate fraction preferably comprises maltodextrin.

The lipid fraction may be comprised in the composition in an amount that corresponds to about 2-100% of the calories of the composition, preferably about 4-50% of the calories of the composition, even more preferred about 5-40% of the calories of the composition may be derived from lipids. The lipid fraction may comprise medium-chain triglycerides (MCT), for example provided in the form of coconut and/or palm kernel oil, preferably in an amount of 60-80 weight-% of the lipid source. A high MCT content will allow that the composition can be easily absorbed by the subject to be treated. The lipid fraction may have a n6:n3 ratio in the range of 1:1-10:1. DHA may be added.

The composition may further comprise another immune boosting agent and/or a pain relieving agent.

A probiotic may be present in the composition. "Probiotic" means microbial cell preparations or components of microbial cells with a beneficial effect on the health or well-being of the host. (Salminen et al. 1999 Trends Food Sci. Technol.

10:107). All probiotic micro-organisms may be used in accordance with the present invention. Preferably, the probiotic may be selected from the group consisting of *Bifidobacterium, Lactobacillus, Lactococcus, Enterococcus, Streptococcus* Ascomycota, Deuteromycota, *Debaryomyces, Kluyveromyces, Saccharoymces, Yarrowia, Zygosaccharomyces, Candida,* and *Rhodotorula*, in particular selected from the group consisting of *Bifidobacterium longum, Bifidobacterium lactis, Bifidobacterium animalis, Bifidobacterium breve, Bifidobacterium infantis, Lactobacillus acidophilus, Lactobacillus casei, Lactobacillus salivarius, Lactococcus lactis, Lactobacillus reuteri, Lactobacillus rhamnosus, Lactobacillus paracasei, Lactobacillus johnsonii, Lactobacillus plantarum, Lactobacillus salivarius, Enterococcus faecium, Saccharomyces cerevisia, Saccharomyces boulardii* and *Lactobacillus reuteri* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium lactis* (2818; CNCM I-3446), *Lactobacillus paracasei* (NCC2461; CNCM I-2116), *Lactobacillus rhamnosus* GG (ATCC53103), *Lactobacillus rhamnosus* (NCC4007; CGMCC 1.3724), *Enterococcus faecium* SF 68 (NCIMB10415), and mixtures thereof.

The composition described in the present invention may also comprise a prebiotic compound. "Prebiotic" means food substances that promote the growth of probiotics in the intestines. They are not broken down in the stomach and/or upper intestine or absorbed in the GI tract of the person ingesting them, but they are fermented by the gastrointestinal microflora and/or by probiotics. Prebiotics are for example defined by Gibson & Roberfroid 1995 J. Nutr. 125:1401).

The prebiotics that may be used in accordance with the present inventions are not particularly limited and include all food substances that promote the growth of probiotics in the intestines. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides (FOS), galacto-oligosaccharides (GOS), isomalto-oligosaccharides, xylo-oligosaccharides, oligosaccharides of soy, glycosylsucrose (GS), lactosucrose (LS), lactulose (LA), palatinose-oligosaccharides (PAO), malto-oligosaccharides (MOS), gums and/or hydrolysates thereof, pectins and/or hydrolysates thereof.

For example a stabilizing agent, a flavouring agent, a colouring agent and/or a lubricant may be added. The composition may contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. They may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

The composition described in the present invention may be administered in an amount sufficient to at least partially cure or arrest the symptoms of thymus atrophy and its complications. An amount adequate to accomplish this is defined as "a therapeutically effective dose". Amounts effective for this purpose will depend on a number of factors known to those of skill in the art such as the severity of the condition and the weight and general state of the patient. In prophylactic applications, compositions according to the invention are administered to a patient susceptible to or otherwise at risk of thymus atrophy in an amount that is sufficient to at least partially reduce the risk of developing thymus atrophy. Such an amount is defined to be "a prophylactic effective dose". Again, the precise amounts depend on a number of patient specific factors such as the patient's state of health and weight.

Preferably, however, the whey or whey protein fraction is administered in daily doses in the range of 5 to 150 g. For example for total enteral nutrition in critically ill patients, the ESPEN guidelines suggest to give 1500 kcal per day in the initial phases of the pathology and around 2000 kcal per day during the recovery phase. Considering that protein content of most products on the market is between 15 and 25% of total calorie content a range between 50 and 100 g of protein per day in the acute phase and between 75 and 125 g protein per day will result.

Nutritional supplements on the other hand would typically contain only 10 to 20 g of proteins.

Those skilled in the art will understand that they can freely combine all features of the present invention described herein, without departing from the scope of the invention as disclosed. In particular, features described for the uses of the present invention may be applied to the composition of the present invention and vice versa.

Further advantages and features of the present invention are apparent from the following Examples and Figures.

FIG. 1. HI induced an atrophy of the thymus which was not corrected by the control enteral diet (HI-CED). Interestingly, the diet containing whey protein hydrolysate (HI-WPH) restored the thymus weight.

EXAMPLE 1

A typical composition that may be used in the present invention is the following:

| Nutrient | per liter |
|---|---|
| Protein (gm): | 40 |
| Protein (% kcal): | 16% |
| Carbohydrate (gm): | 127 |
| Carbohydrate (% kcal): | 51% |
| Fat (gm): | 39 |
| Fat (% kcal): | 33% |
| Free $H_2O$: | 85% |
| Vitamin A (IU): | 4300 (includes approximately 37% Vitamin A activity as beta carotene) |
| Beta-Carotene (mg): | See above |
| Vitamin D (IU): | 272 |
| Vitamin E (IU): | 30 |
| Vitamin K (mcg): | 50 |
| Vitamin C (mg): | 340 |
| Thiamine-B1 (mg): | 2 |
| Riboflavin-B2 (mg): | 2.4 |
| Niacin (mg): | 28 |
| Vitamin B6 (mg): | 4 |
| Folic Acid (mcg): | 540 |
| Pantothenic Acid (mg): | 14 |
| Vitamin B12 (mcg): 8 | 133% |
| Biotin (mcg): | 400 |
| Choline (mg): | 452 |
| Taurine (mg): | 100 |
| L-Carnitine (mg): | 100 |

-continued

| Nutrient | per liter |
|---|---|
| Sodium (mg): | 560 |
| Sodium (mEq): | 24.3 |
| Potassium (mg): | 1500 |
| Potassium (mEq): | 38.5 |
| Chloride (mg): | 1000 |
| Chloride (mEq): | 28.2 |
| Calcium (mg): | 800 |
| Calcium (mEq): | 40 |
| Phosphorus (mg): | 700 |
| Magnesium (mg): | 300 |
| Iron (mg): | 18 |
| Iodine (mcg): | 148 |
| Copper (mg): | 2 |
| Zinc (mg): | 24 |
| Manganese (mg): | 2.8 |
| Selenium (mcg): | 50 |
| Molybdenum (mcg): | 120 |
| Chromium (mcg): | 40 |

EXAMPLE 2

A rat model of HI by fluid percussion was used. Rats were randomized into 3 groups: (1) rats receiving control enteral diet (CED), (2) rats sustaining HI and receiving control enteral diet (HI-CED), and (3) rats sustaining HI and receiving a diet containing whey protein hydrolysate (HI-WPH). The enteral diets were infused continuously during 4 days after the HI and were isocaloric, isonitrogenous and isovolumic. After animal sacrifice, the thymus was removed and weighed. Results are shown in FIG. 1 and in table 1.

TABLE 1

|  | Body weight (g) | Thymus weight (g) | Thymus relative weight (%) |
|---|---|---|---|
| CED | 320 ± 8 | 0.46 ± 0.02$^a$ | 0.14 ± 0.01$^a$ |
| HI-CED | 318 ± 5 | 0.30 ± 0.03$^b$ | 0.09 ± 0.01$^b$ |
| HI-WPH | 339 ± 9 | 0.47 ± 0.04$^a$ | 0.14 ± 0.01$^a$ |

Mean ± SEM; ANOVA + Newman Keuls. (a ≠ b, p < 0.01).

The invention claimed is:

1. A method for maintaining thymus function in a mammal having acute thymus atrophy and that is pregnant or suffers from a disorder selected from the group consisting of cancers, autoimmune disorders, infections, toxication and combinations thereof, the method comprising administering a therapeutically-effective amount of a composition comprising whey or at least one protein fraction thereof to the mammal, wherein the whey protein fraction contains 2-3 weight-% arginine.

2. The method of claim 1, wherein the mammal is an adult.

3. The method of claim 1, wherein the mammal is selected from the group consisting of humans, pets, companion animals and livestock.

4. The method of claim 1, wherein the whey protein fraction is obtained from a source selected from the group consisting of human, bovine, sheep, goat and camel sources.

5. The method of claim 1, wherein the whey is at least in part whey protein hydrolysate having a degree of hydrolysis between 8 and 20%.

6. The method of claim 1, wherein the composition contains minerals in amounts corresponding to no more than 100% of the recommended daily mineral intake per 100 g whey protein.

7. A method for increasing the efficacy of vaccines comprising administering to a mammal that has acute thymus atrophy and has received a vaccine a therapeutically-effective amount of a composition comprising whey or at least one protein fraction thereof, wherein the whey protein fraction contains 2-3 weight-% arginine.

8. The method of claim 1, wherein the whey or the at least one protein fraction thereof comprises about 5-100% of the total calories of the composition.

9. The method of claim 1, comprising a carbohydrate fraction and a lipid fraction.

10. The method of claim 1, wherein the composition also maintains or re-establishes lymphocyte function.

11. The method of claim 1, wherein the composition also boosts the immune system.

12. The method of claim 1, wherein the composition comprises another ingredient selected from the group consisting of immune boosting agent; a probiotic; and a prebiotic compound.

13. The method of claim 1, wherein the composition comprises at least one ingredient selected from the group consisting of a pain relieving agent, a stabilizing agent, a flavoring agent, a colouring agent and a lubricant.

14. A method for improving thymus function in a mammal having acute thymus atrophy and that is pregnant or suffers from a disorder selected from the group consisting of cancers, autoimmune disorders, infections, toxication and combinations thereof, the method comprising the step of administering to the mammal a therapeutically-effective amount of a composition comprising whey or a protein fraction thereof, wherein the whey protein fraction contains 2-3 weight-% arginine.

15. The method of claim 1, wherein the composition is intended for an administration route selected from the group consisting of oral, enteral, topical and parenteral administration.

16. The method of claim 14, wherein the mammal is an adult.

17. The method of claim 14, wherein the composition is intended for a mammal selected from the group consisting of humans, pets, companion animals and livestock.

18. The method of claim 14, wherein the whey protein fraction is obtained from a source selected from the group consisting of human, bovine, sheep, goat and camel sources.

19. The method of claim 14, wherein the whey is at least in part enzymatically hydrolyzed whey protein.

20. The method of claim 14, wherein the composition contains minerals in amounts corresponding to no more than 100% of the recommended daily mineral intake per 100 g whey protein.

21. The method of claim 14, wherein the whey or the at least one protein fraction thereof comprises about 5-100% of the total calories of the composition.

22. The method of claim 14, comprising a carbohydrate fraction and a lipid fraction.

23. The method of claim 14, wherein the composition also maintains or re-establishes lymphocyte function.

24. The method of claim 14, wherein the composition also boosts the immune system.

25. The method of claim 14, wherein the mammal is in a state selected from the group consisting of malnutrition; obesity; immune deficiency; autoimmune disorders; stress; infections; toxication; and combinations thereof.

26. The method of claim 14, wherein the composition comprises another ingredient selected from the group consisting of immune boosting agent; a probiotic; and a prebiotic compound.

27. The method of claim 14, wherein the composition comprises an ingredient selected from the group consisting of a pain relieving agent, a stabilizing agent, a flavoring agent, a colouring agent and a lubricant.

28. The method of claim 14, wherein the composition is intended for an administration route selected from the group consisting of oral, enteral, topical and parenteral administration.

29. The method of claim 1, wherein the mammal is pregnant.

30. The method of claim 1, wherein the mammal suffers from at least toxication.

31. The method of claim 1, wherein the mammal suffers from at least cancer.

32. The method of claim 1, wherein the mammal suffers from at least autoimmune disorder.

33. The method of claim 1, wherein the mammal suffers from at least infection.

* * * * *